United States Patent [19]

Pews et al.

[11] Patent Number: 4,940,821

[45] Date of Patent: Jul. 10, 1990

[54] PREPARATION OF FLUOROPHENOLS

[75] Inventors: R. Garth Pews; James A. Gall, both of Midland, Mich.

[73] Assignee: The Dow Chemical Company, Midland, Mich.

[21] Appl. No.: 325,421

[22] Filed: Mar. 20, 1989

[51] Int. Cl.$^5$ .................. C07C 37/02; C07C 39/27
[52] U.S. Cl. ..................... 568/775; 568/774
[58] Field of Search ................ 568/775, 774

[56] References Cited

U.S. PATENT DOCUMENTS 2,950,325  9/1960  Britton et al. ............... 568/775
4,122,288 10/1978  Christensen et al. ......... 568/775

FOREIGN PATENT DOCUMENTS 0004144  1/1985  Japan ........................ 568/775
0143404  1/1962  U.S.S.R. .................... 568/775
 850888 10/1960  United Kingdom ............ 568/775

OTHER PUBLICATIONS

Yakobson et al. "Aromatic Fluorine Derivatives Dokl. Akad. Nauk SSSR" vol. 141, p. 1395 (1961).

*Primary Examiner*—Werren B. Lone
*Attorney, Agent, or Firm*—Craig. E. Mixan; Ronald G. Brookens

[57] ABSTRACT

Fluorophenols are prepared by heating a chlorofluorobenzene with water in the presence of a copper salt at a pH of from 3.0 to 6.5.

6 Claims, No Drawings

PREPARATION OF FLUOROPHENOLS

FIELD OF THE INVENTION

The present invention relates to the preparation of fluorophenols from the corresponding chlorofluorobenzenes. More particularly, the present invention is directed to the hydrolysis of chlorofluorobenzenes under acidic conditions in the presence of catalytic amounts of copper salts.

BACKGROUND OF THE INVENTION

Fluorophenols are useful intermediates for the manufacture of various industrial products including dyes, agricultural pesticides and lubricants. For example, o-fluorophenol may be chlorinated or brominated to 2-fluoro-4-chlorophenol or 2-fluoro-4-bromophenol, respectively, for use in preparing ((fluorophenoxy)-phenoxy)propionate herbicides as described in U.S. Pat. No. 4,550,192.

Conventional methods of preparing fluorophenols have been based on diazotization routes which involve a series of steps. In British Patent No. 1,433,455, for example, fluorophenols were prepared by (a) diazotizing a fluoroaniline, and (b) decomposing the diazonium salt in the presence of water.

Alternatively, fluorophenols have been prepared by the hydrolysis of the corresponding halofluorobenzenes; see, for example, U.S. Pat. No. 2,950,325, British Patent No. 850,888, Russian Patent No. 143,404, and G. G. Yakobson et al. in *Dokl. Akad. Nauk SSSR*, 141, 1395 (1961) and in *Zh. Obshch. Khim.*, 34, 932 (1964). Typically, these hydrolysis reactions are conducted under basic conditions in the presence of a copper catalyst. Yields are particularly dependent on competing reactions such as reduction and diphenyl ether formation. For all practical purposes, the preparative value of the hydrolysis reaction is limited to bromo derivatives, with the corresponding chlorofluorobenzenes giving little if any product under comparable conditions.

SUMMARY OF THE INVENTION

We have now found that chlorofluorobenzenes can be hydrolyzed to the corresponding fluorophenols under acidic conditions. The present invention is directed to a method for preparing a fluorophenol of the formula

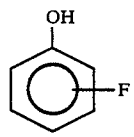

which comprises heating a chlorofluorobenzene of the formula

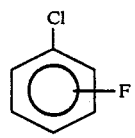

with water in the presence of a copper salt at a pH of from about 3.0 to about 6.5. Surprisingly, the present invention allows for the preparation of fluorophenols from the corresponding chlorofluorobenzense in yields comparable to those attained with the more expensive and less readily available bromofluorobenzenes.

DETAILED DESCRIPTION OF THE INVENTION

The chlorofluorobenzene starting compounds are commercially available materials.

The hydrolysis reaction is carried out in the presence of a copper-containing catalyst. Suitable catalysts include, for example, the oxide, hydroxide, chloride, bromide, iodide, sulfate and acetate salts of copper in either its cuprous (+1) or cupric (+2) oxidation state. The copper-containing catalyst is usually employed in an amount corresponding to from about 0.03 to about 0.25 moles of catalyst per mole of chlorofluorobenzene, although larger proportions can be used.

The hydrolysis reaction is conducted under acidic conditions, for example, at a pH from between about 3.0 to about 6.5, preferably from about 4.5 to about 6.5. Because HCl is generated during the reaction, the pH descrease as the reaction proceeds. In a small scale reaction the pH is conveniently controlled by the addition of an appropriate buffer solution. For example, potassium dihydrogen phosphate has a pH of 4.64. With the addition of the appropriate amount of sodium hydroxide, the resulting pH of the buffer can be conveniently adjusted to any value up to 6.5. Other buffer systems work equally well. In a large scale reaction, the pH could be continuously controlled, for example, by the addition of caustic to a recirculating side stream in which the conditions are such as to allow constant monitoring of the pH.

The hydrolysis reaction of the present invention requires an aqueous system. In most cases, a two-phase system consisting of (a) an aqueous phase containing the copper salt and (b) the chlorofluorobenzene is employed. With the two-phase system, the reaction is conducted with sufficient agitation to maintain a dispersion of reactants. Enough water must be present to effect hydrolysis of the chlorofluorobenzene. Theoretically, at least one mole of water per mole of chlorofluorobenzene is required. In practice, a large excess of water is preferred.

Optionally, the reaction may be conducted in the presence of a phase-transfer catalyst or a surfactant. Such additives can be used in the present reaction in an amount of from about 0.001 to about 0.25 moles per mole of chlorofluorobenzene, preferably from about 0.05 to about 0.1 molar equivalents.

Phase-transfer catalysts are well-known compounds and include (a) quaternary ammonium or phosphonium salts containing 10 or more carbon atoms, and (b) macrocyclic polyethers commonly known as crown ethers. Suitable crown ether catalysts incude 18-crown-6; dicyclo-hexano-18-crown-6; dibenzo-18-crown-6; and 15-crown-5. A related species, tris(3,6-dioxaheptyl)amine is also efficacious. Suitable quaternary phosphonium salts include the tetraalkyl and tetraaryl phosphonium halides, sulfates, etc.

Suitable classes of surfactants include, for example, alkayl sulfonate salts, alkylaryl sulfonate salts, alkylaryl polyether alcohols, fatty acid esters of polyhydric alcohols and the alkylene oxide addition products of such esters.

Optionally, the reaction may be conducted in the presence of antioxidants, such as, for example, sulfur and hydroquinone. Antioxidants can be advantageously employed in an amount from abut 0.001 to about 0.25 moles per mole of chlorofluorobenzene.

The present reaction is conducted at elevated temperatures of from about 225° to about 300° C. The preferred temperature range is from about 250° to about 290° C.

Because the reaction temperatures are above the boiling point of water, the reaction is conducted at pressures at least as great as the autogenous pressure of the mixture of materials at the prescribed temperature, i.e., at pressures sufficient to maintain the water in the reaction mixture substantially in the liquid phase.

In carrying out the present reaction, the chlorofluorobenzene, aqueous buffer, copper salt and any additives, such as phase-transfer catalyst or surfactant, are added to a pressure reactor which is then sealed. The reaction is run at the prescribed temperature to the desired stage of completion at which point the reactor is cooled and carefully opened.

The reaction is preferably run to less than complete conversion to minimize by-products such as diphenyl ethers and reduced starting material. The fluorophenol can be recorvered from the reaction mixture by conventional techniques such as extraction or distillation. Unreacted chlorofluorobenzene can be recovered by similar techniques and recycled.

The following examples illustrate the practice of the present invention and should not be construed as limiting.

EXAMPLE 1

Preparation of o-Fluorophenol

To a 300 milliliter (mL) Hastelloy "C" pressure reactor was added 16.3 grams (g) of o-chlorofluorobenzene (0.125 moles), 135 mL of 1 molar (M) $NaH_2PO_4$ solution to which enough NaOH was added to adjust the pH to 6.5, 5.08 g (0.0125 moles) of tetraphenyl phosphonium bromide and 3.2 g (0.016 moles) of $CuSO_4.5H_2O$. The reactor was sealed and pressure tested. The reaction was stirred for 24 hours (hr) at 250° C. After cooling to ambient temperature, the reactor was carefully opened. The contents of the reactor were acidified with 250 mL of conc. HCl and the organics were extracted into diethyl ether. The extract was analyzed by gas chromatography both alone and in tandem with mass spectrometry. The reaction mixture gave the following analysis:

| | |
|---|---|
| o-fluorophenol(o-FP) | 0.023 moles |
| o-chlorofluorobenzene (o-CFB) | 0.047 moles |
| fluorobenzene (FB) | 0.012 moles |
| o-chlorophenol | trace |
| unknowns | |

EXAMPLE 2

Preparation of o-Fluorophenol o-Fluorophenol (o-FP) was prepared from o-chlorofluorobenzene (o-FCB) in a series of runs performed according to the procedure described in Example 1. The reactions were conducted in a 300 mL or a 600 mL Hastelloy "C" pressure reactor equipped with an efficient mechanical stirrer. The pH was adjusted at the start of the reaction by the use of mono- and di-basic salts of phosphoric acid and their mixtures with acids or bases. For example, a buffer of pH=4.64 would consist of a solution of $KH_2PO_4$. A buffer of pH=5.5 or pH=6.5 could be prepared by treatment of the pH=4.64 buffer with a solution of either $K_2HPO_4$ or NaOH. Reaction conditions and results are summarized in Table I. The buffers are listed by their amounts (mL), molarity (M) and pH.

TABLE I

PREPARATION OF o-FLUOROPHENOL

| Run | Temp °C. | Time hr | moles o-CFB | Buffer mL | M | pH | Cat(g) | Reaction Composition o-FP | o-CFB | FB | % mass bal. | % conv. | % yield |
|---|---|---|---|---|---|---|---|---|---|---|---|---|---|
| 1a | 250 | 24 | 0.125 | 135 | 1 | 6.5 | $CuSO_4.5H_2O$(3.2) | 0.024 | 0.061 | 0.004 | 76.8 | 51.2 | 37.5 |
| 2 | 250 | 24 | 0.125 | 135 | 1 | 6.5 | $CuSO_4.5H_2O$(3.2) | 0.048 | 0.053 | 0.003 | 83.2 | 57.6 | 66.7 |
| 3 | 250 | 48 | 0.250 | 270 | 1 | 5.5 | $CuSO_4.5H_2O$(6.4) | 0.046 | 0.053 | 0.006 | 42.0 | 78.8 | 23.4 |
| 4 | 250 | 24 | 0.250 | 270 | 1 | 4.64 | $CuSO_4.5H_2O$(6.4) | 0.045 | 0.066 | 0.007 | 47.2 | 73.6 | 24.5 |
| 5 | 250 | 24 | 0.250 | 270 | 1 | 5.5 | $CuSO_4.5H_2O$(6.4) | 0.062 | 0.134 | 0.003 | 79.6 | 46.4 | 53.4 |
| 6 | 270 | 24 | 0.250 | 270 | 1 | 5.5 | $CuSO_4.5H_2O$(6.4) | 0.078 | 0.124 | 0.016 | 87.2 | 50.4 | 61.9 |
| 7b | 250 | 2 | 0.250 | 200 mL | | $H_2O$ | $Cu(OAc)_2.2H_2O$(16.8) | 0.021 | 0.155 | 0.014 | 76.0 | 38.0 | 22.1 |
| 8 | 250 | 12 | 0.250 | 270 | 1 | 5.5 | $CuSO_4.5H_2O$(6.4) | 0.048 | 0.153 | 0.010 | 84.4 | 38.8 | 49.5 |
| 9 | 250 | 24 | 0.250 | 270 | 1 | 5.5 | $CuSO_4.5H_2O$(54.5) | 0.046 | 0.006 | 0.135 | 74.8 | 97.6 | 18.9 |
| 10c | 250 | 24 | 0.250 | 270 | 1 | 5.5 | $Cu(OAc)_2.2H_2O$(5) | 0.033 | 0.150 | 0.005 | 75.2 | 40.0 | 33.0 |
| 11 | 250 | 24 | 0.250 | 270 | 1 | 5.5 | $CuSO_4.5H_2O$(54.5) | 0.035 | 0.130 | 0.041 | 82.4 | 48.0 | 29.2 |
| 12 | 250 | 24 | 0.250 | 270 | 1 | 4.64 | $CuSO_4.5H_2O$(6.4) | 0.060 | 0.140 | 0.015 | 86.0 | 44.0 | 54.5 |
| 13 | 250 | 24 | 0.250 | 270 | 1.5 | 5.5 | $CuSO_4.5H_2O$(6.4) | 0.084 | 0.120 | 0.013 | 86.8 | 52.0 | 64.6 |
| 14 | 270 | 48 | 0.250 | 270 | 1.5 | 5.5 | $CuSO_4.5H_2O$(6.5) | 0.087 | 0.099 | 0.012 | 79.2 | 60.4 | 57.6 |
| 15 | 250 | 24 | 0.250 | 270 | 2 | 4.64 | $CuSO_4.5H_2O$(6.4) | 0.067 | 0.137 | 0.015 | 87.6 | 45.2 | 48.9 |
| 16 | 270 | 24 | 0.250 | 270 | 2 | 4.64 | $CuSO_4.5H_2O$(6.4) | 0.074 | 0.103 | 0.020 | 78.8 | 58.8 | 50.3 |
| 17 | 270 | 24 | 0.250 | 270 | 1.5 | 5.5 | Cuo(2.55) | 0.107 | 0.070 | 0.016 | 77.2 | 72.0 | 59.4 |
| 18 | 290 | 24 | 0.250 | 270 | 2 | 4.64 | $CuSO_4.5H_2O$(6.4) | 0.075 | 0.110 | 0.014 | 79.6 | 56.0 | 53.6 |
| 19 | 270 | 24 | 0.250 | 270 | 1.5 | 4.64 | CuO(2.55) | 0.098 | 0.081 | 0.015 | 77.6 | 67.6 | 58.8 |
| 20 | 290 | 24 | 0.250 | 270 | 1.5 | 4.64 | Cuo(2.55) | 0.079 | 0.132 | 0.007 | 87.2 | 47.2 | 66.9 |
| 21 | 270 | 24 | 0.250 | 270 | 1.5 | 4.64 | CuO(5.1) | 0.106 | 0.095 | 0.017 | 87.2 | 62.0 | 68.4 |
| 22 | 290 | 24 | 0.250 | 270 | 1.5 | 4.64 | CuO(2.55) | | 0.086 | 0.013 | 76.8 | 65.6 | 56.7 |
| 23 | 250 | 24 | 0.250 | 270 | 1.5 | 4.64 | CuO(2.55) | 0.093 | 0.137 | 0.008 | 86.0 | 45.2 | 61.9 |
| 24 | 270 | 24 | 0.250 | 270 | 1.5 | 4.64 | $Cu_2O$(4.59) | 0.014 | 0.050 | 0.043 | 71.2 | 80.0 | 42.5 |
| 25 | 270 | 24 | 0.250 | 270 | 1.5 | 4.64 | $Cu_2O$(4.59) | | 0.063 | 0.045 | 80.0 | 74.8 | 48.1 |
| 26d | 270 | 24 | 0.250 | 270 | 1.5 | 4.64 | CuBr(4.56) | 0.090 | 0.136 | 0.009 | 82.4 | 45.6 | 28.9 |
| 27e | 270 | 24 | 0.250 | 270 | 1.5 | 4.64 | CuBr/CuO(4.56/2.55) | 0.033 | 0.098 | 0.033 | 70.4 | 60.8 | 21.1 |
| 28f | 270 | 24 | 0.250 | 270 | 1.5 | 4.64 | $CuSO_4.5H_2O$(6.4) | 0.002 | 0.155 | 0.014 | 94.4 | 38.0 | 70.5 |
| 29g | 270 | 24 | 0.250 | 270 | 1.5 | 4.64 | CuO(2.55) | 0.067 | 0.162 | 0.007 | 90.4 | 35.2 | 64.8 |
| 30h | 270 | 24 | 0.250 | 270 | 1.5 | 4.64 | CuO(2.55) | 0.057 | 0.083 | 0.029 | 80.8 | 66.8 | 53.9 |
| 31i | 270 | 24 | 0.250 | 270 | 1.5 | 4.64 | CuO(2.55) | 0.090 | 0.075 | 0.006 | 55.6 | 70.0 | 31.1 |
| 32j | 270 | 24 | 0.250 | 270 | 1.5 | 4.64 | CuO(2.55) | 0.058 | 0.121 | 0.021 | 92.0 | 51.6 | 68.2 |

TABLE I-continued

| | | | | | | | | | Reaction Composition | | | % mass | % | % |
|---|---|---|---|---|---|---|---|---|---|---|---|---|---|---|
| | Temp | Time | moles | Buffer | | | | | | | | | | |
| Run | °C. | hr | o-CFB | mL | M | pH | Cat(g) | | o-FP | o-CFB | FB | bal. | conv. | yield |
| 33k | 270 | 24 | 0.250 | 270 | 1.5 | 4.64 | CuO(2.55) | | 0.088 | 0.098 | 0.015 | 77.0 | 60.8 | 52.6 |
| 34l | 270 | 24 | 0.250 | 270 | 1.5 | 4.64 | CuO(2.55) | | 0.080 | 0.183 | 0.004 | 89.2 | 26.8 | 53.7 |
| 35m | 270 | 12 + 12 | 0.250 | 270 | 1.5 | 4.64 | CuO(2.55) | | 0.036 | 0.195 | 0.001 | 90.4 | 22.0 | 54.5 |
| 36n | 270 | 12 + 12 | 0.260 | 270 | 1.5 | 4.64 | CuO(2.55) | | 0.030 | 0.081 | 0.022 | 74.0 | 69.2 | 50.3 |
| 37o | 250 | 12 + 12 | 0.250 | 270 | 1.5 | 4.64 | CuO(2.55) | | 0.091 | 0.108 | 0.016 | 84.8 | 56.8 | 62.0 |
| 38 | 250 | 12 | 0.250 | 270 | 1.5 | 4.64 | CuO(2.55) | | 0.088 | 0.178 | 0.007 | 94.0 | 28.8 | 69.4 |
| 39p | 250 | 12 | 0.250 | 270 | 1 | 7.8(6.0) | CuO(2.55) | | 0.050 | 0.105 | 0.016 | 80.8 | 58.8 | 55.9 |
| 40q | 250 | 24 | 0.250 | 270 | 1 | 6.4(4.2) | CuO(2.55) | | 0.081 | 0.100 | 0.013 | 85.2 | 60.0 | 66.6 |
| 41q | 250 | 12 | 0.250 | 270 | 1 | 6.8(4.8) | CuO(2.55) | | 0.100 | 0.114 | 0.012 | 85.2 | 54.4 | 64.0 |
| 42q | 250 | 6 | 0.250 | 270 | 1 | 6.5(5.4) | CuO(2.55) | | 0.087 | 0.153 | 0.009 | 89.6 | 38.8 | 63.9 |
| 43q | 235 | 12 | 0.250 | 270 | 1 | 6.5(5.4) | CuO(2.55) | | 0.062 | 0.189 | 0.002 | 89.2 | 24.4 | 54.1 |
| 44q | 250 | 12 | 0.250 | 270 | 1 | 6.7(5.1) | CuO(2.55) | | 0.032 | 0.130 | 0.005 | 86.8 | 48.8 | 70.0 |
| 45q | 250 | 12 | 0.250 | 270 | 1 | 6.6(4.4) | CuSO$_4$.5H$_2$O(7.97) | | 0.082 | 0.159 | 0.003 | 90.0 | 36.4 | 69.2 |
| 46qr | 250 | 6 + 6 | 0.250 | 270 | 1 | 6.4(6.1) | CuO(2.55) | | 0.063 | 0.158 | 0.004 | 87.6 | 36.8 | 56.5 |
| 47qs | 250 | 6 + 6 | 0.250 | 270 | 1 | 6.7(6.1) | CuO(2.55) | | 0.057 | 0.137 | 0.005 | 84.8 | 45.2 | 61.9 |
| 48qt | 250 | 12 + 12 | 0.250 | 270 | 1 | 6.4(5.1) | CuO(2.55) | | 0.070 | 0.068 | 0.012 | 74.4 | 72.8 | 57.7 |
| 49q | 270 | 12 | 0.250 | 270 | 1 | 6.7(?) | CuO(2.55) | | 0.105 | 0.099 | 0.008 | 84.8 | 60.4 | 69.5 |

(a) 5.08 g tetraphenylphosphonium Bromide added;(b) 15 g HOAc, 16.5 g NaOAa added;(c) 135 mL MeOH added;(d) 25.5 g NaBr added;(e) 25.5 g NaBr added. Also, two catalysts were used;(f) 3.26 g Zonyl FSA (fluorinated alkyl carboxylate salt) added;(g) 3.26 g ARQUAD 12-50(dodecyltriethylammonium chloride) added;(h) 4.68 g Tetraphenylphosphonium chlorida added;(i) 0.16 g Sulfur added;(j) 0.55 g Hydroquinone added;(k) 0.16 g Fluorad FC-95 (potassium fluoroalkylsulfonate) added;(l) 10.2 g Sulfur added;(m) 0.16 g Sulfur added. 39.0 g K$_2$HPO$_4$ added after 12 hours;(n) Additional 2.55 g CuO and 10 g K$_2$HPO$_4$ added after 12 hours;(o) Additional 10 g K$_2$HPO$_4$ added after 12 hours;(p) 0.25 mol of K$_2$HPO$_4$ added at the start of the reaction;(q) 0.13 mol of K$_2$HPO$_4$ added at the start of the reaction;(r) added 10 g K$_2$HPO$_4$ after 6 hours;(s) added 2.55 g CuO after 6 hours;(t) added 2.55 g CuO and 15 g K$_2$HPO$_4$ after 12 hours.

EXAMPLE 3

Preparation of m-Fluorophenol m-Fluorophenol ws prepared from m-chlorofluorobenzene in a series of runs performed according to the description of Example 2. Reaction conditions and results are summarized in Table II.

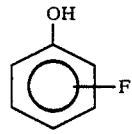

TABLE II

PREPARATION OF m-FLUOROPHENOL

| Run | Temp °C. | Time hr | moles m-CFB | Buffer mL | M | pH | Cat(g) | Reaction Composition m-FP | m-CFB | FB | % mass bal. | % conv. | % yield |
|---|---|---|---|---|---|---|---|---|---|---|---|---|---|
| 50 | 250 | 12 | 0.25 | 270 | 1 | 6.5(5.6) | CuO | 0.062 | 0.155 | 0.002 | 87.6 | 38.0 | 65.3 |
| 51(u) | 250 | 24 | 0.25 | 270 | 1 | 6.5 | CuO | 0.113 | 0.065 | 0.004 | 72.8 | 74.0 | 61.1 |
| 52 | 250 | 12 | 0.25 | 270 | 1 | 6.5(5.5) | CuSO$_4$.5H$_2$O | 0.046 | 0.185 | 0.001 | 92.8 | 26.0 | 70.8 |
| 53 | 270 | 12 | 0.25 | 270 | 1 | 6.5(4.8) | CuO | 0.102 | 0.108 | 0.002 | 84.8 | 56.8 | 71.8 |
| 54 | 270 | 12 | 0.25 | 270 | 1 | 6.5(4.1) | CuSO$_4$.5H$_2$O | 0.082 | 0.137 | 0.002 | 88.4 | 45.2 | 72.6 |

(u) added 20.0 g K$_2$HPO$_4$ & 2.55 g CuO after 12 hours.

EXAMPLE 4

Preparation of p-Fluorophenol p-Fluorophenol was prepared from p-chlorofluorobenzene in a series of reactions performed as described in Example 2. Reaction conditions and results are summarized in Table III.

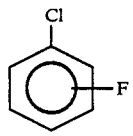

TABLE III

PREPARATION OF p-FLUOROPHENOL

| Run | Temp °C. | Time hr | moles p-CFB | Buffer mL | M | pH | Cat(g) | Reaction Composition p-FP | p-CFB | FB | % mass bal. | % conv. | % yield |
|---|---|---|---|---|---|---|---|---|---|---|---|---|---|
| 55 | 270 | 12 | 0.25 | 270 | 1 | 6.6(3.8) | CuO | 0.120 | 0.080 | 0.004 | 81.6 | 68.0 | 70.6 |
| 56 | 270 | 12 | 0.25 | 270 | 1 | 6.7(4.1) | CuO | 0.110 | 0.084 | — | 77.6 | 69.4 | 66.3 |

What is claimed is:

1. A process for preparing a fluorophenol of the formula which comprises heating a chlorofluorobenzene of the formula with water at a temperature from about 225° to about 300° C. in the presence of a copper-containing catalyst in either the cuprous or cupric oxidation state at a pH of from about 0.3 to about 6.5.

2. The process of claim 1 in which the copper-containing catalyst is selected from the group consisting of the oxide, hydroxide, chloride, bromide, iodide, sulfate and acetate in either the cuprous or cupric oxidation state.

3. The process of claim 1 in which the fluorine is ortho.

4. The process of claim 1 in which the fluorine is meta.

5. The process of claim 1 in which the fluorine is para.

6. The process of claim 1 in which the pH is maintained between about 3.0 and about 6.5 by means of a buffer.

* * * * *